United States Patent [19]
Saini et al.

[11] Patent Number: 5,521,101
[45] Date of Patent: May 28, 1996

[54] MONITORING BIOELECTROCHEMICAL REACTIONS AND NOVEL MEDIA FOR BIOELECTROCHEMICAL REACTIONS

[75] Inventors: Selwayan Saini, Barking; Anthony P. F. Turner, Newport Pagnell, both of United Kingdom

[73] Assignee: Cranfield University, Cranfield, England

[21] Appl. No.: 112,670

[22] Filed: Aug. 26, 1993

[30] Foreign Application Priority Data

Aug. 28, 1992 [GB] United Kingdom ............ 9218376

[51] Int. Cl.$^6$ ................................ G01N 33/533
[52] U.S. Cl. ...................... 456/518; 435/4; 435/7.1; 435/7.9; 435/176; 435/177; 435/180; 435/287.1; 435/287.7; 435/287.9; 436/152; 436/530; 436/531; 436/535; 422/82.01; 422/82.02; 422/90; 422/98; 204/403; 204/410; 204/414; 204/421; 204/431
[58] Field of Search .................... 204/403, 410, 204/411–412, 414–415, 418, 421, 431; 422/82.01–82.02, 90, 98; 427/2; 435/4, 7.1, 7.9, 14, 25, 26, 176, 177, 180, 288, 291; 436/518, 530, 531, 535, 152

[56] References Cited

U.S. PATENT DOCUMENTS

| | | | |
|---|---|---|---|
| 4,020,830 | 5/1977 | Johnson et al | 128/2 E |
| 4,049,503 | 9/1977 | Becker et al. | 204/1 |
| 4,517,291 | 5/1985 | Seago | 435/14 |
| 4,525,704 | 6/1985 | Campbell | 340/632 |
| 4,581,336 | 4/1986 | Malloy et al. | 435/176 |
| 4,655,880 | 4/1987 | Liu | 204/1 T |
| 4,744,954 | 5/1988 | Campbell et al. | 422/98 |
| 4,830,939 | 5/1989 | Lee et al. | 429/192 |
| 4,894,253 | 1/1990 | Heineman et al. | 427/36 |
| 4,975,175 | 12/1990 | Karube et al. | 204/403 |
| 5,082,550 | 1/1992 | Rishpon et al. | 204/403 |
| 5,091,299 | 2/1992 | Turner | 435/4 |
| 5,200,334 | 4/1993 | Dunn et al. | 435/182 |
| 5,205,920 | 4/1993 | Oyama et al. | 204/403 |
| 5,229,282 | 7/1993 | Yoshioka et al. | 435/177 |

FOREIGN PATENT DOCUMENTS

| | | |
|---|---|---|
| 4032599 | 4/1992 | Germany . |
| WO88/01299 | 2/1988 | WIPO . |

OTHER PUBLICATIONS

B. Oliver et al, "Electrochemical Reactions, Enzyme Electrocatalysis, and Immunoassay Reactions in Hydrogels", Biosens. Technol. [Proc. Int. Symp.] 1989 (Pub 1990) pp. 117–135.

Chemical Abstract 115(13):131128 published 30 Sep. 1991 re Oliver et al, "Electrochemical reactions . . . in hydrogels" in Biosens. Technol., 1989 (Publ. 1990) pp. 117–135.

Karube, "A Methane Gas Sensor Based On Oxidizing Bacteria", Analytica Chimica Acta, vol. 135 (1982), pp. 61–67.

Hikuma, "Ammonia Electrode With Immobilized Nitrifying Bacteria", Anal. Chem., vol. 52, 1980, pp. 1020–1024.

Goodson, "Application of Immobilized Enzymes to Detection and Monitoring", *Enzyme engineering*, vol. 2, 1974, pp. 393–400.

Oliver, "'Solid–State' Voltammetry of a Protein in a Polymer Solvent", J. Am. Chem. Soc., vol. 110, 1988, pp. 2321–2322.

Turner, "Enzyme–Based Carbon Monoxide Sensors", *Microbial Gas Metabolism*, 1985, pp. 161–170.

Turner, "Carbon Monoxide: Acceptor Oxidoreductase From . . . ", Analytica Chimica Acta, vol. 163, pp. 161–174.

Karube, "Amperometric Determination of Ammonia Gas with Immobilized Nitrifying Bacteria", Anal Chem., vol. 53, 1981, pp. 1852–1854.

Hikuma, "Amperometric Determination of Acetic Acid With Immobilized Trichosporon Brassicae", Analytica Chimica Acta, vol. 109, 1979, pp. 33–38.

Hikuma, "Microbial Electrode Sensor for Alcohols", Biotechnology and Bioengineering, vol. XXI, 1979, pp. 1845–1853.

Okada, "Microbial Sensor System Which Uses Methylomonas sp. for the Determination of Methane", Applied Macrobiology and Biotechnology, vol. 12, 1981, pp. 102–106.

Okada, "NO$_2$ Sensor which Uses Immobilized Nitrite Oxidizing Bacteria", Biotechnology and Bioengineering, vol. XXV, 1983, pp. 1641–1651.

Guibault, "Determination of Formaldehyde with an Enzyme–Coated Piezoelectric Crystal Detector", Anal. Chem., vol. 55, 1983, pp. 1682–1684.

*Primary Examiner*—Carol A. Spiegel
*Attorney, Agent, or Firm*—Lee, Mann, Smith, McWilliams, Sweeney & Ohlson

[57] ABSTRACT

A method of determining an analyte in the gaseous or vapour phase and in which a bioreceptor or biomimic is retained at an electrode. The bioreceptor or biomimic is preferably retained at a support at the electrode which comprises a solid or gel matrix of an electrolyte, especially organic salt electrolytes. Electrochemical detection of analytes in this way has several advantages over existing methods which rely on solution monitoring. For example gas sensors can be prepared for monitoring an analyte by the occurrence of a reaction with a bioreceptor or biomimic, in addition to monitoring the presence of toxins due to inhibition of the bioreceptor or biomimic reaction. Furthermore, the invention enables gas or vapour analyte monitoring with increased sensitivity and speed and greater stability of the sensors can be achieved. The invention also relates to novel media for carrying out bioelectrochemical reactions.

17 Claims, 9 Drawing Sheets

MONITORING BIOELECTROCHEMICAL REACTIONS AND NOVEL MEDIA FOR BIOELECTROCHEMICAL REACTIONS

The present invention relates to bioelectrochemical reactions. In particular, the invention relates to a method for monitoring an analyte using an electrochemical cell to determine the reaction of a gaseous or vapour substrate. The invention also relates to novel media for carrying out bioelectrochemical reactions and their use in enzyme electrodes.

It is well known to use an enzyme electrode to perform and monitor bioelectrochemical reactions. Generally such reactions are carried out in aqueous solution. It is also known to use enzyme electrodes in organic or micro-aqueous solvents, as described in WO89/04364 for detecting reactions of substrates in the liquid phase.

Methods are known for monitoring reactions in the gaseous phase. The applicability of gas sensors for monitoring gaseous analytes becomes clear on consideration not only of the number of toxic or hazardous gases originating from natural or anthropogenic sources, but also applications in process control. Conventional gas sensor devices are non-biological and generally employ optical or electrochemical metal oxide semi-conductor devices. However, these types of instruments can in some instances be insensitive and may display relatively poor selectivity for an analyte to be detected in complex mixtures, such as organic vapours. Though a higher level of electronic sophistication may provide some compensation for these drawbacks, this can lead to elevated production costs.

Amperometric electrochemical gas sensors are also known. They generally operate at lower electrical power than semi-conductor gas sensors and work at room temperature. Again, these sensors may lack selectivity for a particular analyte.

One example of such a non-biological gas sensor is described in DE-A-4032599. In that reference, a three dimensional polyurethane matrix containing an electrolyte and a catalyst is positioned at a test electrode. The current generated between the test electrode and a second, counter electrode is dependent upon the partial pressure of the test components.

However this reference does not relate to bioelectrochemical reactions and therefore the specific requirements for maintaining bioreceptors or biomimic in the solid or semi-solid phase and which will still enable contact with the gaseous substrate is Hot addressed.

In order to try to increase selectivity, nonbiological sensors may employ a carefully chosen liquid electrolyte that offers some form of selection for a targeted analyte. For example, parameters such as solubility of gases, electrolyte pH, chemical reactions or complex formation between solutes and analyte can be used to vapour the dissolution of one form of an analyte species.

However, an alternative method for increasing selectivity in sensors is to incorporate a biological catalyst into the sensor. Such sensors are known but the gaseous analyte is usually required to dissolve into a bulk mobile liquid phase prior to detection. For examples, see I. Karube et al, Analytica Chimica Acta, 135 (1982) 61–67; M. Hikuma et al, Anal. Chem. (1980) 52, 1020–1024; and L. H. Goodson and W. B. Jacobs, in Enzyme Engineering, Vol. 2, Plenum Press, New York, 1974, p 393 edited by E. K. Pye and L. B. Wingard Jr. The liquid electrolyte used in this type of apparatus is generally defined by the physiological requirements of the biocatalyst and factors such as solution pH, ionic strength etc must be taken into consideration if the conditions are to remain appropriate for biocatalysis.

Investigations into electrochemistry have been carried out. In J. Chem. Soc. 1988, 110, p 2321–2322 by B. N. Oliver et al report investigations into the solid state voltammetry of a protein and a polymer solvent. The redox protein, cytochrome C was dissolved in a semi-rigid polymer film. On humidifying or adding liquid micro droplets to thin ionically conducting films, the electron transfer and diffusion properties of cytochrome C in the semi-rigid polymer film were reported. The authors suggested that this research could be used to develop solid phase biosensors or in solid state enzyme catalysis but no further developments were reported.

Some gas sensors which use biological reactions are known. For example, WO88/01299 describes a method and apparatus for detecting chemical compounds in the gaseous phase. An enzyme in conjunction with a colour indicator responsive to pH, oxidation, or other chemical input of the compound to be detected in the gas phase is immobilised on an organic or inorganic solid support and dehydrated under controlled conditions. When the enzyme is exposed to a gas containing the substance of interest, the colour change occurs. The exemplified solid support for the enzyme is micro-crystalline cellulose. However, this reference does not relate to the use of an electrochemical cell to monitor the reaction and therefore the problem of providing a suitable electrolyte for such monitoring is not encountered.

In U.S. Pat. No. 4,525,704, an enzymatic toxic gas sensor is described. It comprises a buffer reservoir containing a buffer solution which operates to maintain the enzyme in its active state, the enzymes are immobilised by covalent bonding to glass beads. In this device, the substrate for reaction with the enzyme is provided in the apparatus as a substrate soaked filter paper. In the presence of an analyte which is a toxic gas, the electrochemical reaction of the liquid phase substrate with the enzyme is inhibited.

In Microbial Gas Metabolism edited by R. K. Poole and C. S. Daw published by Academic Press 1985, pages 161 to 170, A. P. F. Turner et al describe a carbon monoxide sensor which responds to carbon monoxide both in solution and as a gas. The sensor is described in more detail in Analytica Chimica Acta, 163 (1984) 161–174. In these studies the reaction of enzyme and substrate occurs in liquid phase.

Furthermore, as is described, there are problems regarding stability of the apparatus and more stable methods are required to produce commercially useful devices.

However, electrochemical gas sensors based on liquid electrolyte share the inherent shortcomings of liquid systems: limited shelf life due to solvent evaporation, electrode corrosion and loss of sensor components. Electrode corrosion reactions may generate gases that can damage seals and eventually cause electrolyte leakage.

Although enzyme electrodes are well known, currently no useful method has been described which will enable monitoring an analyte using an electrochemical cell where the analyte is not an inhibitor for the enzyme activity, and where the enzyme is not held in the liquid phase.

The present inventors have found alternative media for monitoring a gaseous or vapour phase analyte using a sensing electrode of an electrochemical cell. These novel media can be used to provide sensors which overcome the problems of the prior art and enable improved stability and longevity of the device.

The present inventors have found that it is possible to dispense with the contact solvent medium which is used to form the electrolyte/enzyme/electrode interface in present devices. The inventors have found novel methods for retaining the electrolyte and biological catalyst at the electrodes and maintaining operability.

According to one aspect of the present invention, there is provided a method for detecting an analyte in the gaseous or vapour phase comprising contacting a gaseous or vapour analyte with a sensing electrode of an electrochemical cell, a bioreceptor or biomimic being retained at a support at the sensing electrode and the support comprising an electrolyte, so that a substrate contacts the bioreceptor or biomimic and reacts, generating an electrical response; and measuring the electrical response of the cell, the response being relatable to the concentration of the analyte and wherein the bioreceptor or biomimic is in the solid or semi-solid phase.

Thus a method is provided for monitoring bioelectrochemical reactions in the gaseous phase which is useful for detecting inhibitors for the bioreceptor or biomimic but more particularly is also useful for monitoring reactions where the analyte is not a toxin for the bioreceptor or biomimic, and the electrical response detected is due to a reaction occuring, not due to inhibition. This considerably broadens the field of application for gas sensors which can be used to detect various gases by means of electrochemical monitoring. In a preferred embodiment of the invention therefore, the electrical response of the cell increases with exposure to an increasing concentration of analyte.

In liquid solution biocatalytic electrochemistry, solution ions, reaction substrate and product can pass in to and out of a material matrix, whether the system uses a porous electrode structure or whether the material matrix encompasses an electrode body. In a solution medium, the biocatalyst is in contact with freely mobile liquids. This invention enables there to be no bulk solution contact with the bioreceptor or biomimic at the support.

It has been found that the solvent medium can therefore be left out altogether, leaving an ionically conducting matrix with active biological component in direct contact with the gaseous or vapour phase. It was found that electrochemical reactions could be effected by gaseous species diffusing to and undergoing reaction at the electrode and that intimate contact of biological components, such as enzymes with the ionic matrix could be achieved so that the electrochemical reaction could be coupled to biochemical reactions of gaseous reactants.

The bio-receptor can be any biological molecule which will bind to a reactant and will produce a detectable electrochemical reaction. A biomimic is a synthetically prepared chemical analogue of a biological receptor for example, synzymes. Examples of bioreceptors are antibodies, binding proteins and biological catalysts such as enzymes.

The bioreceptor or biomimic will generally be a biological catalyst such as an enzyme. When the bioreceptor or biomimic is an enzyme, or synthetic equivalent thereof, the substrate can be an enzyme-substrate or an enzyme-cofactor. The bioreceptor or biomimic is in the solid or semi-solid state. This expression is intended to mean that it is not in the liquid phase, in particular, not in aqueous solution. The bioreceptor or biomimic will generally be in a substantially dehydrated state. In order to maintain activity of the bioreceptor or biomimic, it has been found that a hydration shell is needed around the bioreceptor or biomimic. This is necessary to retain the three-dimensional structure of the bioreceptor or biomimic which is essential to maintain its activity. Thus, even though the bioreceptor or biomimic may be substantially dehydrated, it will be sufficiently hydrated to maintain the required degree of hydration to maintain activity, and will not be anhydrous.

The invention is particularly useful for monitoring reaction in which the substrate for the reaction with the bioreceptor or biomimic is derived from the analyte. One possibility is that the analyte is the substrate for the bioreceptor or biomimic. Further possibilities are that the bioreceptor or biomimic catalyses the conversion of an analyte into a product which undergoes an electrochemical reaction directly at the electrode; or that the bioreceptor or biomimic is one which can effect oxidation or reduction of the substrate, possibly with the intervention of a mediator, and is thus involved in the transfer of electrons between the substrate and the electrode; or that the analyte reacts at the support at the electrode with for example an enzyme to produce a substrate for binding with the bioreceptor or biomimic.

Alternatively the analyte may be an inhibitor or precursor for an inhibitor for the bioreceptor or biomimic.

Various solid or semi-solid alternatives to the use of bulk liquid solvents as electrochemical media which can be used are known. Inorganic materials which have been investigated are B-alumina and silver salts. Of the organic solid or gel alternatives, suitable media are hydrogels, ionomers and polyelectrolytes, or solvating polymers.

As explained by M Madou and T Otagawa in solid state ionics (1988) vol. 28–30, p 1653–1659 hydrogels can be regarded as aqueous electrolyte solutions trapped in a polymeric matrix. The impedance exhibited using such media is typically similar to that for trapped aqueous electrolyte solutions. Evaporation of the solvent is slowed by the polymer matrix and can be further slowed by the incorporation of hygroscopic materials facilitating ion movement within the gel. One example is described in DE-A-4032599 (discussed above) where a three-dimensional polymeric matrix of polyurethane is formed and which contains an organic conductor salt. A solid or gel electrolyte may also be formed from ionomers and polyelectrolytes which contain anionic (eg $—CF_2SO_3$) or cationic (eg $—R_3N^+$) groups bound to the polymer chain which act as counter ions to small unbound and potentially mobile ions. One suitable example is Nafion which is a copolymer of Teflon or polytetrafluoroethylene (PTFE) and polysulphenylfluoride vinyl ether containing sulphonic acid groups chemically bound to a fluorocarbon backbone.

Solvating polymers may also be used. Here the dry polymer itself has the ability to dissolve certain salts and support ionic mobility. Solvating ability is an essential pre-requisite for fast ion conduction in a dry polymer. Examples of this type of material include poly(propylene oxide) (PPO) with dissolved lithium salts. (see P. J. Smith, Electrochemical Science and Technology of Polymers (1987) p 293 edited by R. G. Linford, Elsevier London.)

In use, the condition at the support medium should be appropriate to maintain activity of the bioreceptor or biomimic.

Whilst solid or gel electrolyte support media such as enzyme-redox mediated gel, hydroxy ethyl cellulose and solid polymer electrolyte enzyme gel may be used in the present invention, they may suffer from problems of either falling ionic conductivity or poor biocompatibility over relatively short periods of time. In the present invention, novel reaction media for bioelectrochemical reactions have also been developed which provide an improved media for bioelectrochemical reactions and in particular provide improved media for use at an enzyme electrode for use in a sensor.

According to a further aspect of the invention, also provided is a novel support medium for a bioelectrochemical reaction comprising a solid or gel matrix electrolyte, a biomimic or bioreceptor for the reaction being retained at the support medium and the substrate for the reaction being contactable with the support to produce the reaction.

In contrast to the previous solid or gel alternatives to bulk liquid electrolyte media, the novel solid or gel media of the present invention are not based on a polymeric matrix structure and are substantially free of organic polymeric material. Instead they are structures formed by the electrolyte itself. The media of the present invention are thought to be in the form of a semi-solid, semicrystalline matrix having a substantially stable structure. They are producable by preparing a solution of the electrolyte and drying. Thus, the support structure consists essentially only of electrolyte.

The novel media provide significant advantages because the ionically conducting materials are not in solution. The reduced water environment increases markedly the thermostability of the biocatalyst at elevated temperatures. Furthermore, the novel media are suitable for use not only with liquid phase reactants, in particular those in non-aqueous or micro-aqueous non-polar liquids but also with gaseous or vapour phase reactants and Diffusivities in the gas phase are orders of magnitude higher than in solution and therefore more sensitive and faster monitoring can be achieved using such media. The heightened sensitivity enables quantitative apparatus to be produced, the response being related to the molar amount of analyte in the test gas or vapour.

These media can therefore advantageously be used in sensors, in particular gas sensors. Many gaseous analytes display poor solubility in solution which can lead to decreased sensitivity whereas the novel media of the present invention reduce this problem. In addition, the electrolyte matrix may be selected for a specific analyte of interest and therefore when used in a sensor, increase device sensitivity.

Further, such gas sensors which rely upon the use of non-liquid electrolytes may not suffer from leaching of sensor components as encountered in conventional liquid phase sensors since the ionically conducting matrix is only contacted by gaseous phase that delivers the analyte to the sensing element.

The novel support media of the invention are able to maintain activity of the bioreceptor or biomimic; provide electrical conductivity; and are sufficiently permeable to enable the reactant for the reaction with the bioreceptor or biomimic, to reach the bioreceptor or biomimic and react.

It has been found that on formation of a matrix of an electrolyte according to the invention, the structure of the matrix, being a semi-crystalline solid, tends to lock in the necessary water molecules to maintain the hydration shell around the bioreceptor or biomimic. Thus, the novel support media of the present invention are substantially free from water but will contain a low concentration of water which is at least sufficient to maintain the required hydration shell around the bioreceptor or biomimic. Thus, the matrix will not be anhydrous.

Regarding the electrical conductivity of these novel support media, it is postulated that this is due to mobility of hydrogen and hydroxyl ions and/or buffer ions within the matrix. However, we do not wish to be limited to this theory.

The matrix is also sufficiently permeable to allow the substrate to contact the bioreceptor or biomimic and react. Thus, the mass transfer properties through the matrix enable the gas to permeate and contact the bioreceptor or biomimic.

Preferably, the permeability to the reactant remains constant or substantially constant.

The solid or gel matrix can be prepared by firstly forming a solution of the electrolyte salt in a solvent. The solution of the salt for preparing the matrix may be in an organic or aqueous solvent which does not deactivate the bioreceptor or biomimic. On drying, the electrolyte matrix forms. Preferably drying is carried out at room temperature.

Generally the solution will be a concentrated solution as this reduces the drying time required, although the support media can be prepared using any concentration of solution. The solvent can be any solvent which can be evaporated to enable drying to form the solid or gel electrolyte matrix.

Preferably drying is carried out at room temperature. Preferably, a buffer is also included in the solution of electrolyte salt to provide appropriate conditions for the activity of the bioreceptor or biomimic. Any other additive necessary to maintain the activity of the bioreceptor or biomimic may be incorporated at this stage.

An electron mediator compound and optionally also the bioreceptor or biomimic itself may be incorporated into the solution prior to drying. Where the bioreceptor or biomimic is included, the drying temperature must not be so high as to lose activity of the bioreceptor or biomimic and the solvent must be selected accordingly. Preferably the drying temperature should be below 37° C., most preferably below 30° C.

The electrolyte salt may also act as a buffer salt or electron mediator. In such cases, the electrolyte salt may fulfill the dual functions of forming the electrolyte matrix and providing buffer or mediator, respectively.

Alternatively, the bioreceptor or biomimic may be arranged at the support in an outer layer, for example, by preparing a separate solution of bioreceptor or biomimic which can then be cast onto the pre-prepared solid or gel matrix and dried.

The bioreceptor may even be formed as a lower layer, in contact with the support material which may be formed over the bioreceptor or biomimic.

The bioreceptor or biomimic is as described above.

Suitable inorganic salts for forming the solid or gel matrix comprise any inorganic salt which will retain stability and sufficient moisture to provide the required hydration shell for the bioreceptor or biomimic. Preferred components comprise buffer salts such as sodium phosphate and salts which may also act as an electron mediator such as potassium ferrocyanide.

More preferably however the matrix will be formed from an organic salt electrolyte. Particularly preferred are quaternary ammonium salts such as tetraalkylammonium salts, in particular tetrabutylammonium perchlorate, tetrabutylammonium toluene-4-sulphonate, tetrabutylammonium methane sulphonate, tetrabutylammonium phenol borate, tetraethylammonium tetrafluoroborate, tetrabutyl ammonium chloride and tetrabutylammonium iodide. These salts are particularly preferred because it has been found that they produce relatively stable matrices which maintain a relatively constant internal water content. A particularly preferred salt is tetrabutyl ammonium toluene-4-sulphonate.

Where it is found that the matrix tends to dehydrate to an extent where the hydration shell of the bioreceptor and or biomimic may be lost, it can be advantageous to use a hygroscopic salt. Tetrabutylammonium toluene-4-sulphonate is an example of such a salt. Alternatively, a hygroscopic material may also be included in the media. Examples of suitable hygroscopic salts are lithium salts such as lithium chloride. These additives may be incorporated into the matrix by adding to the solution used for forming the support media.

The novel media may be employed in the determination of an analyte by a sensor, in particular in the gaseous or vapour phase.

According to a further aspect of the invention, there is provided a sensing electrode comprising a conductor, a support associated with the conductor and a bioreceptor or biomimic retained at the support, the support comprising a solid or gel matrix of an electrolyte, as described above.

Furthermore, the present invention also provides an electrochemical sensor comprising sensing and counter electrodes, means for permitting access of a substrate to the sensing electrode, the sensing electrode comprising a conductor, a support which comprises a solid or gel matrix of an electrolyte associated with the conductor and a bioreceptor or biomimic immobilised or retained on or adjacent to the support. The solid or gel matrix of an electrolyte is as described above. Preferably during use, the water-content of the solid or gel matrix is kept substantially constant.

In particular the invention relates to sensors for monitoring analytes in the gaseous phase.

According to a further aspect of the invention, there is also provided a method for detecting an analyte in the gaseous or vapour phase comprising contacting a gaseous or vapour analyte with a sensing electrode of an electrochemical cell, a bioreceptor or biomimic being retained at a support at the sensing electrode so that a substrate contacts the bioreceptor or biomimic and reacts generating an electrical response; and measuring the electrical response of the cell, the response being relatable to the concentration of the analyte, and wherein the support comprises a solid or gel matrix of an electrolyte.

As above, the analyte may be the substrate. Alternatively, the bioreceptor or biomimic may catalyse the conversion of the analyte into a product which then undergoes an electrochemical reaction directly at the electrode. A further alternative is that the bioreceptor or biomimic is one which can effect oxidation or reduction of the substrate, possibly with the intervention of a mediator, and is thus involved in the transfer of electrons between the substrate and the electrode; or that the analyte reacts at the support with, for example an enzyme to produce a reaction product which binds with the bioreceptor or biomimic.

Alternatively the analyte may be an inhibitor or may form an inhibitor for the bioreceptor or biomimic. The media may also be used for reactions in which a current is applied to produce a reaction within the media.

Suitable bioreceptors or biomimics for use with the methods and apparatus of the present invention are as described above. However, bioreceptors or biomimics which are inhibited by an analyte or reaction product of an analyte may also be used in particular, where the support comprises a solid or gel matrix of an electrolyte. Examples include: sulphite oxidase for detecting sulphur dioxide; polyphenol oxidase for detecting phenolic vapours, an oxygenase enzyme (or biomimic) for detecting methane; cytochrome P450 or preferably synthetic analogues, for detecting hydrocarbons such as camphor; nitrate reductase for detecting NOx gases; carbon monoxide oxidoreductase for detecting carbon monoxide; cytochrome oxidass for detecting cyanide; TNT oxidoreductase for detecting TNT; and enzymes which may metabolise the analyte or anitbodies, for example for pesticides may be used.

It has been found that where the bioreceptor or biomimic is incorporated into the support media-forming electrolyte solution, prior to drying to form the support with retained bioreceptor or biomimic, a lag phase i.e. time lapse, may occur between exposure of the support media to the gaseous or vapour analyte and the electrochemical response. The present inventors have postulated that the structure of the support media may be affected by the analyte itself.

It has been found that this problem can be reduced and may be substantially overcome by reducing the thickness of the electrolyte layer of the gel support media or by casting the layer of bioreceptor or biomimic in a second step, as an outer layer on the pre-prepared matrix.

It is thought that when the support is formed by incorporating the bioreceptor or biomimic into the solution for forming the matrix, the rate-limiting step in the reaction of the bioreceptor or biomimic and substrate is the diffusion of the analyte through the matrix which enables contact of the substrate with the bioreceptor or biomimic. That is, generally the sensor should be operated at a voltage more negative than the voltage of the reaction peak being observed. In contrast, when the bioreceptor or biomimic is cast in a second stage as an outer layer, the diffusion barrier is reduced. However, the bioreceptor or biomimic in an outer layer cast onto the pre-prepared matrix may have reduced stability due to its relatively more exposed position. Therefore, preferably the bioreceptor or biomimic is formed within the matrix by incorporation into the solution for forming the matrix and the support at the sensing electrode comprising the matrix is preferably formed as a thin layer.

The bioreceptor or biomimic may be formed in an initial step on or in the electrode structure and covering with a layer of matrix.

The matrix layer is generally less than 1 mm thick. Preferably the matrix layer should have a thickness of no greater than 100 μm, most preferably no greater than 50 μm.

Any electrochemical cell is suitable for use in the sensors of the present invention. Preferably the electrodes are provided by a microvoltammetric electrode. Such an electrode is advantageous because it can alleviate cell resistance to analytically useful levels.

When the gas sensor is being used to detect an inhibitor for the bioreceptor or biomimic it may be decided that the biosensor should not operate in the limiting current range and that instead, the rate limiting step may be the rate of catalysis. In this case, for an inhibitor analyte the rate of inhibition will provide the rate limiting step and not the rate of mass transfer.

The gas sensor of the present invention may be a two electrode sensor in which there is a sensing electrode and a counter electrode which also acts as a reference electrode. However if the counter electrode tends to polarise with current, preferably the sensor will be a three electrode sensor comprising the sensing electrode, and separate counter and reference electrodes respectively.

In a preferred embodiment of the invention, an electrochemical sensor as described above is provided in which the sensing electrode is provided with a porous membrane which substantially covers the electrolyte matrix thereby limiting the rate of mass transfer of the gaseous or vapour analyte to the enzyme/electrolyte interface to provide a rate limiting step in the monitoring.

Preferably, the rate of access of analyte is restricted to the electrode in the sensor, by a diffusion barrier, as described in GB 1571282, under conditions such that the electrode is operating in a so-called limiting current region. In the limiting current region, the concentration of the analyte at the electrode surface is essentially zero. The limiting current, will then be proportional to the flux of the analyte which will be a function of the partial pressure of the analyte in the gas being sensed.

Such a diffusion barrier may produce the additional advantage that it will result in increased stability of the matrix and therefore in the performance of the gas sensor, in particular by reducing dehydration of the matrix.

Some examples of electrodes and monitoring of bioelectrochemcial reactions are now described with reference to the accompanying drawings.

EXAMPLES

Figure 1:
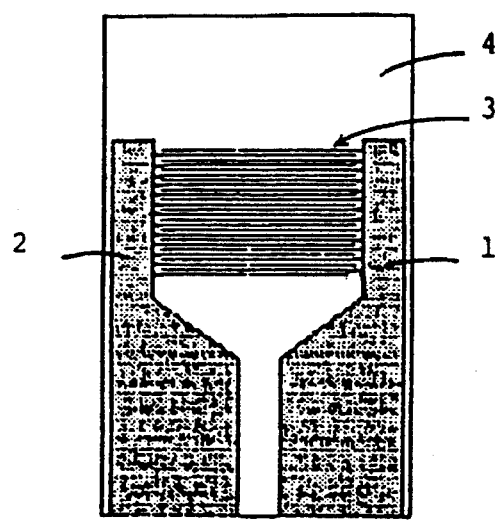
FIG. 1 illustrates an interdigitated microband electrode used in the examples given below.

All experiments were performed at room temperature (18° C.) using a gold microband electrode having 50 pairs of interdigitated electrodes with finger width of 15 μm and finger spacing of 15 μm. The acoustic aperture of the electrode used was 4800 μm and the electrode thickness, 1000 Å± 500 Å at a sufficiently cathodic potential. FIG. 1 illustrates the interdigitated microband electrode used (supplied by Microsensor Systems, Kentucky, USA) in which 1 and 2 represent the sensing electrode and the combined counter and quasi-reference electrode (CC + QRE), respectively. The interdigitated regions of the electrodes are clearly visible at 3. The electrode is supported by quartz 4.

Example 1.

Reaction of Gaseous $H_2O_2$ with Horseradish Peroxidase Electron Mediator Gels Cast Onto an Array of Interdigitated Microband Array Electrodes.

In this example, we demonstrate the reaction of inorganic $H_2O_2$ gas with the enzyme, horseradish peroxidase [E.C. 1.11.1.7] and an electron mediator. The enzyme is oxidised by hydrogen peroxide and utilises the one electron donator, potassium hexacyanoferrate (II). The resulting oxidised form of mediator is then reduced at a gold microband electrode as described above.

In this example, the gel that formed from a solution of enzyme, electron mediator and citric acid buffer was utilised as an ionically conducting matrix with incorporated biocatalyst. The reduced ohmic drop at the microelectrodes facilitated the monitoring of the biocatalytic electrochemical reaction within the gel matrix.

Experimental

Figure 2:
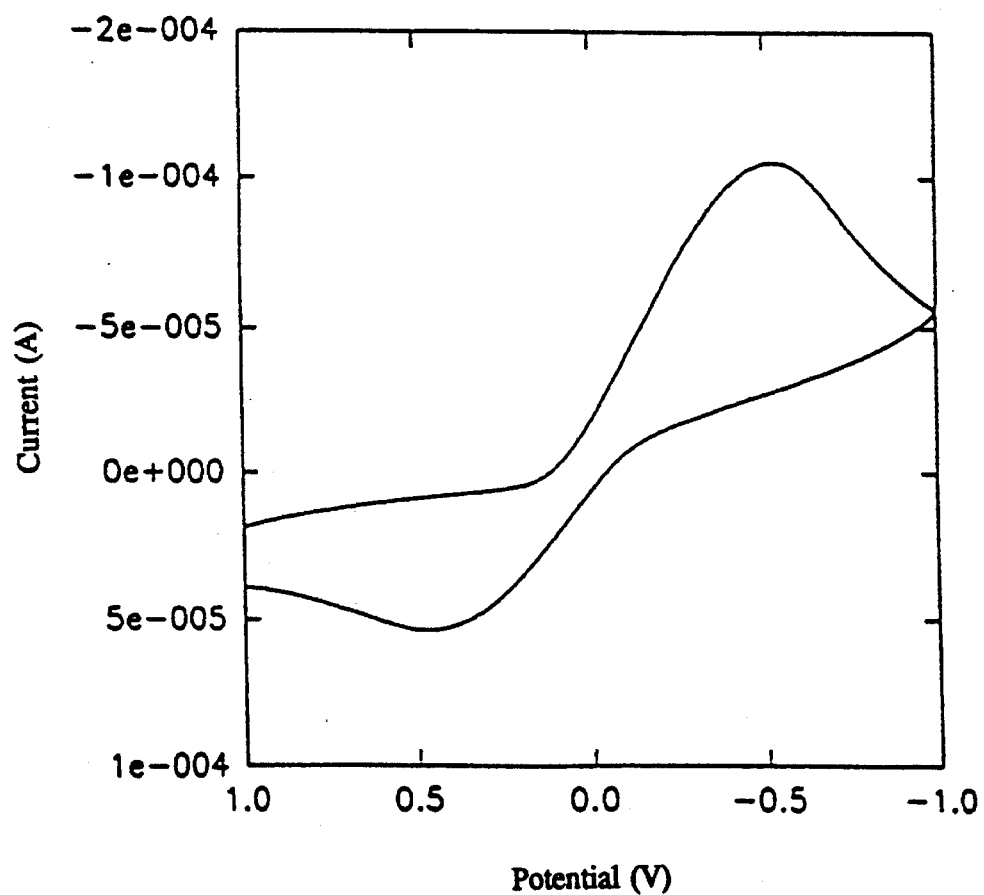
FIG. 2 shows a cyclic voltammogram at 0.2 V/s of a gel consisting of horseradish peroxidase, potassium hexacyanoferrate (II) and citric acid buffer after 10 minutes drying.

The enzyme-mediator gels were prepared as follows. Horseradish peroxidase (2 mg) was added to a 100 μl solution of potassium hexacyanoferrate (II) (0.05M) in citric acid buffer (0.1M, pH 6.5). The mixture was vigorously stirred for one minute on a rotator. A volume of 5 μl of the resulting solution was then deposited onto the microelectrode array section of the gold electrodes and allowed to dry in air at room temperature for 10 minutes. Following this period, the enzyme-mediator solution had formed a gel that was immobile on electrode inversion. A cyclic voltammogram at 0.2 V/s in which the potential was cycled from +1 V to −1 V versus the combined counter and quasi-reference electrodes, revealed two peaks corresponding to the one electron oxidation and reduction of the electron mediator. The results are illustrated in FIG. 2. Of interest was the reduction peak at approximately −0.5 V versus the combined counter and quasi-reference electrode.

To investigate the activity of the biocatalytic electrochemical media, amperometric experiments were performed in the presence of gaseous $H_2O_2$ substrate. The potential of the indicator electrodes was set at −0.6 V versus the CC + QRE for the reduction of the oxidised form of mediator following the enzyme reaction with $H_2O_2$. After an initial steady state equilibrium current had been attained, a 20 mλ beaker containing 10 mλ 0.8 M $H_2O_2$ in water was periodically presented to the electrode at a distance of 5 mm from the liquid surface.

Figure 3:
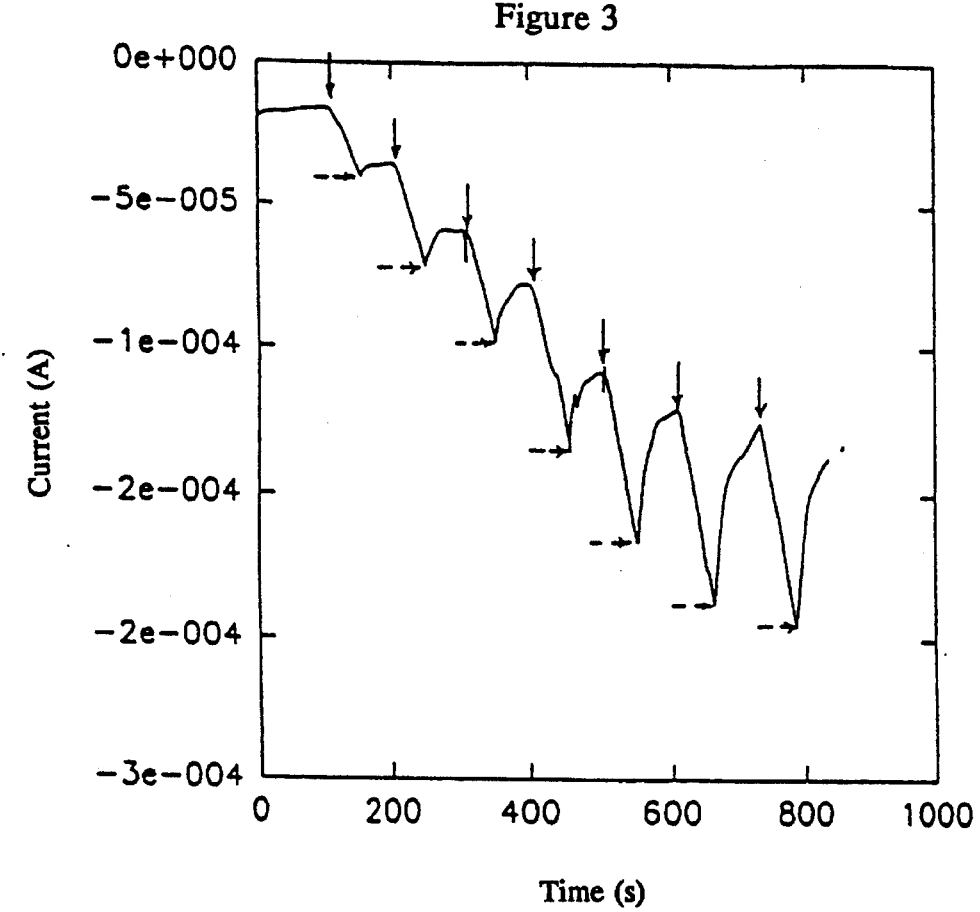
FIG. 3 shows an amperometric trace of horseradish peroxidase/hexacyanoferrate (II)/citric acid buffer gel electrode.

The results are illustrated in FIG. 3. The solid arrows indicate exposure to gaseous $H_2O_2$. The broken arrows indicate no exposure to gaseous $H_2O_2$. The increase in cathodic current represented the biocatalytic electrochemical reaction of the enzyme and mediator and gaseous $H_2O_2$. Control electrodes devoid of enzyme and/or mediator produced much smaller current increases and it was concluded that these were a result of conductivity changes within the gel matrix induced by the substrate.

The enzyme-mediator gels were active for approximately 45 minutes at room temperature after which time negligible current increases were recorded; this loss of current probably arose from the reduced ionic conductivity in the gel matrix as a result of solvent loss to the atmosphere.

Example 2.

Reaction of Phenol Vapours with Polyphenol Oxidase at a Solid Polymer Electrolyte Cast Onto an Array of Interdigitated Microband Electrodes.

In this example, a solid polymer electrolyte, Nafion, was utilised as an ionically conducting matrix in the gas phase onto which the enzyme polArphenol oxidass [E.C. 1.14.18.1] was precipitated. Nafion is a copolymer of Teflon or tetrafluorethylene (PTFE) and polysulfonylfluoride vinyl ether containing sulfonic acid groups. The sulfonic acid groups are chemically bound to a fluorocarbon backbone. The indicator reaction was that of p-cresol vapours with polyphenol oxidass and the subsequent reduction of quinone product at the gold microband working electrodes at a cathodic potential.

This experiment and all of the examples using pcresol outlined below were also carried out replacing pcresol with phenol. In each case, the results obtained were qualitatively the same, but greater current magnitudes were obtained.

Experimental

A 0.83 wt. % solution of Nafion in isopropanol was sonicated for 5 minutes. A clean microband electrode was then vertically dip coated into this solution for a period of 15 minutes. The electrode was immersed to the extent that all the microbands were completely covered by Nafion solution. After a further 5 minute period of air drying at room temperature, the Nafion coated electrode was placed in a drying cabinet at 72° C. for 30 minutes. Following a cooling period of 5 minutes on the bench, the modified electrode was ready for use. Examination of the electrode surface revealed visible interference patterns indicative of an uneven surface coverage of the polymer electrolyte.

Figure 4:
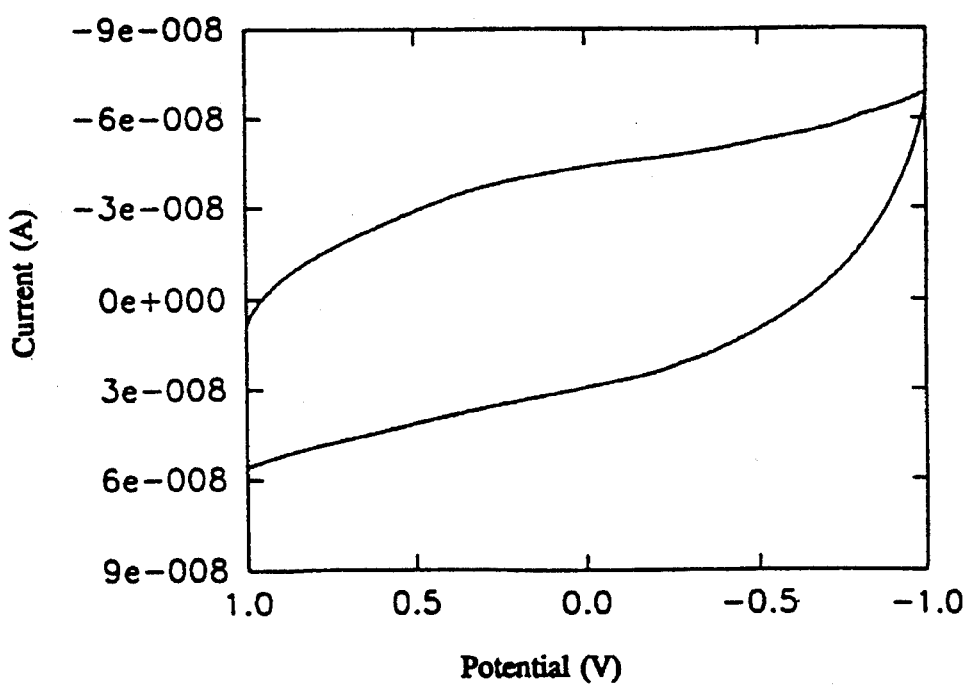
FIG. 4 shows a cyclic voltammogram at 0.2 V/s of a Nation modified microband electrode at 18° C. in air.

FIG. 4 shows the results of a cyclic voltammogram at 0.2 V/s of the modified electrode in air at 18° C. The potential was cycled from +1 V to −1 V versus the CC + QRE.

Figure 5:
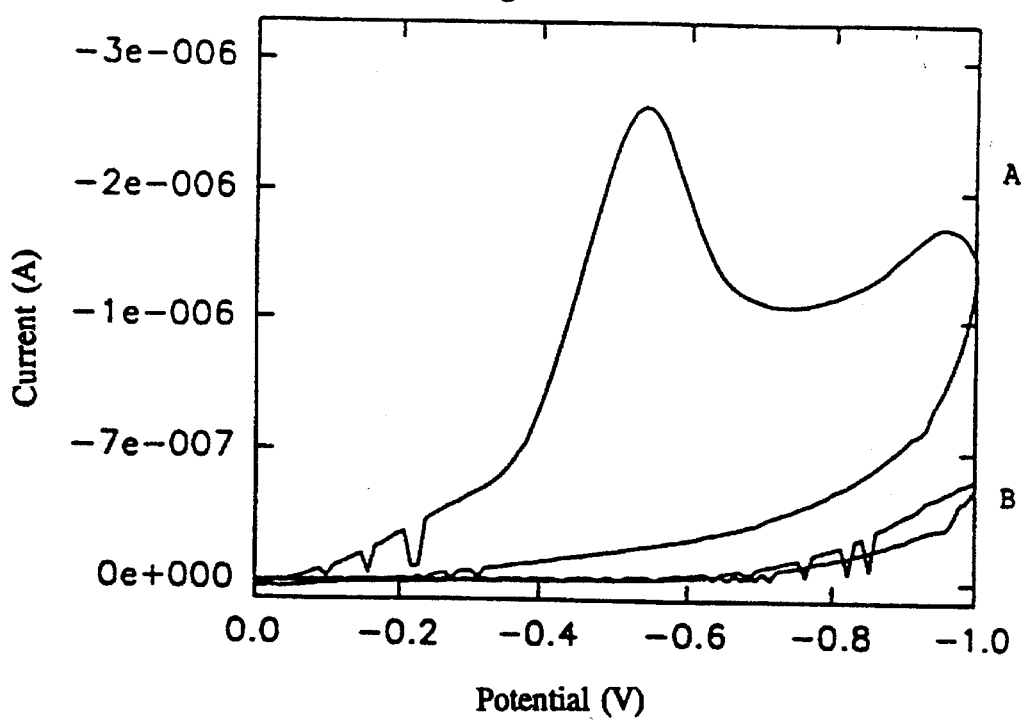
FIG. 5 shows cyclic voltammograms at 0.005 V/s of (A) polyphenol oxidase-Nafion electrode and (B) Nation only electrode in the presence of p-cresol vapours.

A solution of polyphenol oxidase (1 mg/100 μl) in sodium phosphate buffer (0.1 M, pH 7) was then prepared and vigorously stirred on a rotator for 2 minutes. A 5 μλ volume of the enzyme solution was then carefully deposited onto the microarray section of the modified electrode and allowed to dry for 15 minutes. After this period, a gel had formed on the electrode that was immobile on electrode inversion. A small glass bottle (35 mm diameter and 35 mm length) containing 500 mg p-cresol crystals was then presented to the electrode. The modified electrode penetrated the neck of the glass bottle to a depth of 5 min. Cyclic voltammograms at 0.005 V/s with and without p-cresol exposure were then recorded. The results are illustrated in FIG. 5. (A) represents the results with the polyphenol oxidase-Nafion electrode and (B) represents the results obtained with the Nafion only electrode in the presence of p-cresol vapours. The potential was cycled from 0 V to −1 V versus the CC + QRE. The clear reduction peak at approximately −0.550 V versus the CC + QRE correspond to the reduction of the quinone product of the enzyme reaction with p-cresol vapour.

Figure 6:
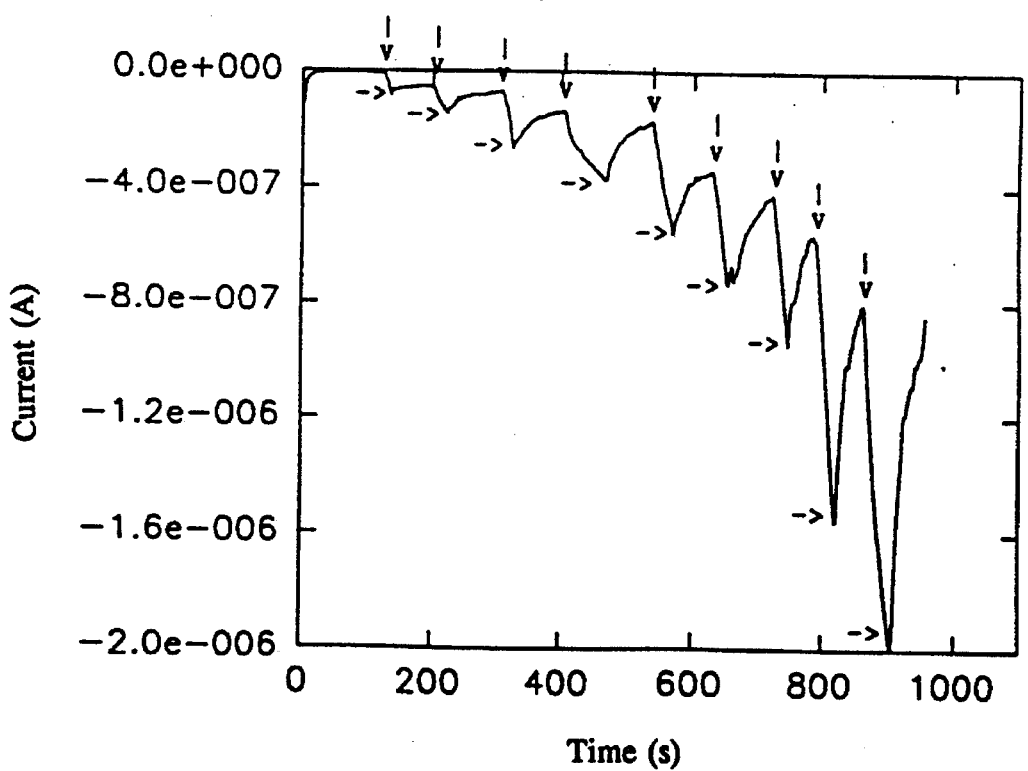
FIG. 6 shows an amperometric trace of Nafion-polyphenol oxidase electrode with approximately 100 second exposures to p-cresol with similar time intervals of no exposure.

Amperometric experiments were then carried out which involved 100 second exposures to phenol vapours with a similar period of no exposure. FIG. 6 shows the amperometric trace of Nafion-polyphenol oxidass electrode with approximately 100 second exposures to p-cresol with similar time intervals of no exposure. The vertical arrows indicate the start of the periodic exposures. The horizontal arrows indicate no exposure. The potential of the working electrodes was −0.650 V versus the CC + QRE. Control electrodes devoid of enzyme yielded small current increases on exposure to p-cresol.

Steady state equilibrium currents were usually obtained within 30–60 seconds. A relatively small current increase was seen in the absence of enzyme, presumably a result of conductivity changes induced by the phenol vapour on the polymer film.

Enzyme-Nafion modified electrodes were only biocatalytically active for approximately 30 minutes. The enzyme was presumed to be inactivated by the acidic groups of the Nafion polymer and/or excessive dehydration. However, the Nafion coated electrode continued to maintain ionic conductivity for at least 28 hours at room temperature after initial preparation. In the absence of Nafion, enzyme gels were not ionically conductive after approximately 25 minutes.

Example 3.

Reaction of Phenol Vapours with Polyphenol Oxidase Incorporated into a Gel of Hydroxethyl Cellulose Cast Onto an Array of Interdigitated Microband Electrodes.

Hydroxyethyl cellulose (HEC) is a water soluble material based on the cellulose polymer structure. In this example, a gel formed by HEC and Hepes buffer was utilised as a biocompatible ionic matrix. The indicator reaction was identical to Example 2.

Experimental

Figure 7:
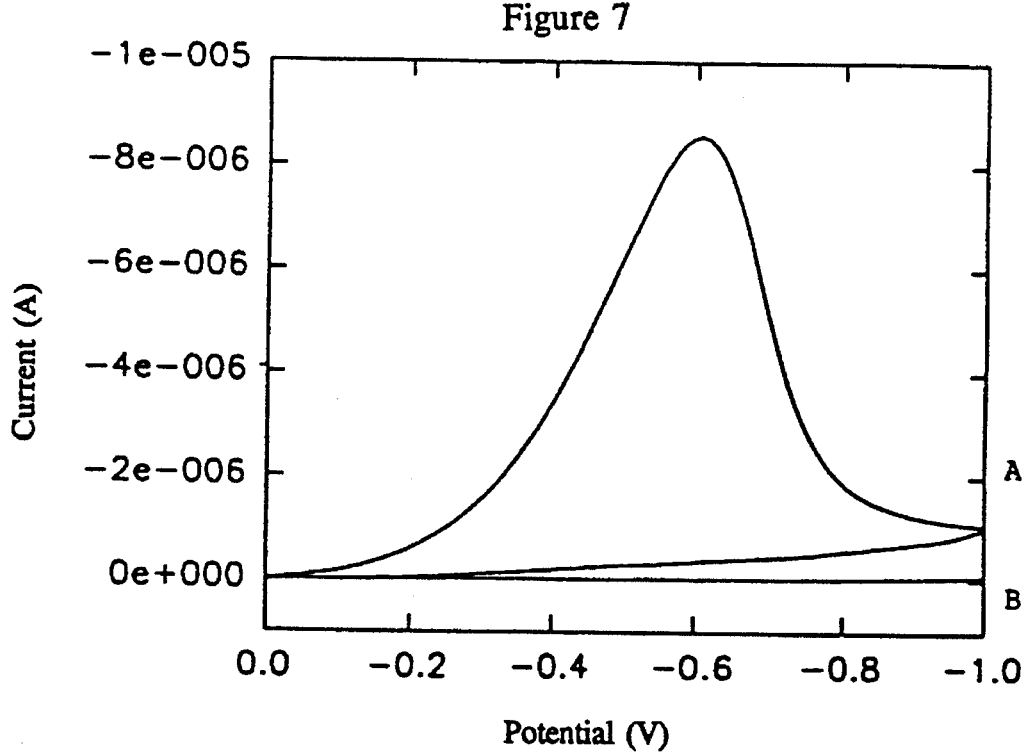
FIG. 7 shows a cyclic voltammogram at 0.005 V/s of (A) hydroxyethyl cellulose-polyphenol oxidase electrode and (B) hydroxyethyl cellulose only electrode in the presence of pcresol vapours.

A 2.5% w/v solution of HEC in Hepes buffer (pH 7, 0.1 M) was prepared and stored at 4° C. for 24 hours prior to use. An enzyme-HEC polymer solution (1 mg/100 μl) was prepared and a volume of 5 μl deposited onto the microband array section of the electrode. After a drying period of 15 minutes, a gel had formed that was immobile on electrode inversion. Cyclic voltammograms at 0.005 V/s with the potential cycled from 0 V to −1 V versus the combined counter and quasi-reference electrodes in the presence and absence of p-cresol vapours revealed a distinct peak at approximately −0.6 V versus the combined counter and quasi reference electrodes corresponding to the reduction of the quinone product of the enzyme reaction with p-cresol. FIG. 7 shows the cyclic voltammogram at 0.005 V/s of (A) hydroxyethyl cellulose-polyphenol oxidase electrode and (B) hydroxyethyl cellulose only electrode in the presence of pcresol vapours.

Figure 8:
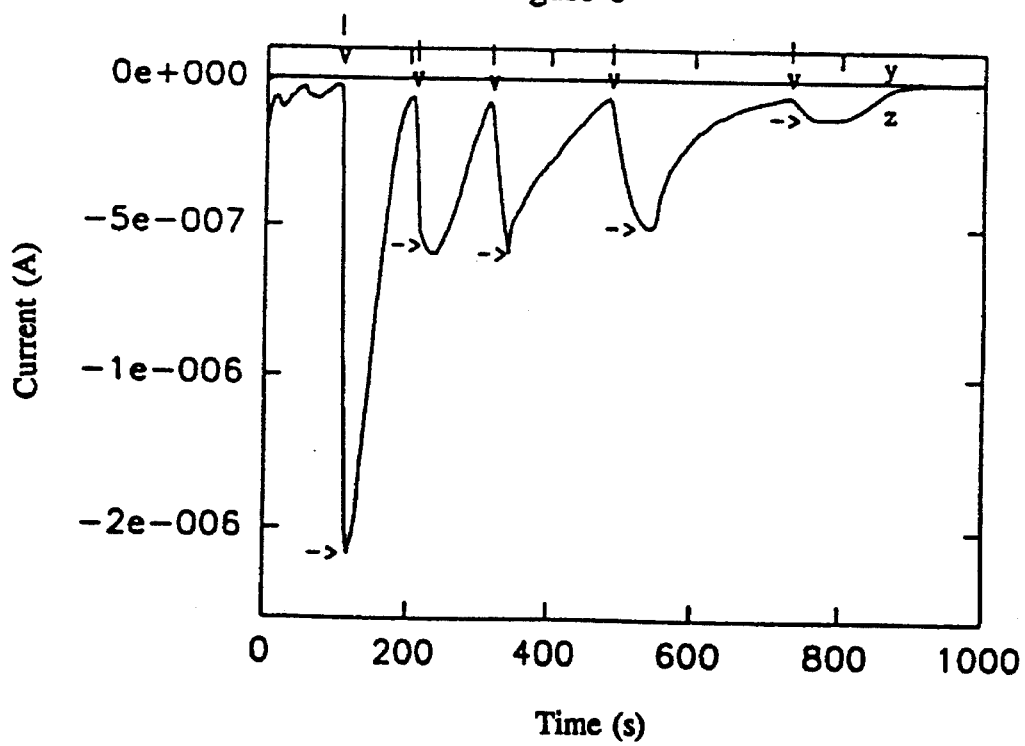
FIG. 8 shows an amperometric trace of (A) hydroxyethyl cellulose-polyphenol oxidase gel electrode and (B) hydroxyethyl cellulose only gel electrode.

Amperometric experiments of the HEC-enzyme gel electrodes involved poising the potential of the working electrodes at −0.7 V versus the CC + QRE. After a drying period of 15 minutes, the gel electrode was periodically exposed to p-cresol vapours. Steady state equilibrium currents were normally obtained in approximately 100 seconds. The current response on exposure to p-cresol was in the region of 30 seconds. Non-steady state response currents were obtained on continued periodic exposure to p-cresol. These results are illustrated in FIG. 8 which shows the amperometric trace of (A) hydroxyethyl cellulose polyphenol oxidass gel electrode and (B) hydroxyethyl cellulose only gel electrode. The solid arrows indicate pcresol exposure; broken arrows indicate no exposure. The potential of the working electrodes was −0.7 V versus the CC + QRE.

HEC-enzyme gels rapidly lost ionic conductivity after 30 minutes. On placing the gel electrode after 30 minutes drying time into a stirred solution of phosphate buffer (pH 7, 0.1 M) and adding dissolved p-cresol, amperometric current increases were once again observed indicating active incorporated enzyme.

Despite active enzyme, the HEC-enzyme electrode configuration suffered from reduced ionic conductivity after 30 minutes, presumably as a result of solvent loss to the atmosphere.

Novel Support Media Facilitating Biocatalytic Electrochemical Reactions in the Gaseous Phase Enzyme-redox mediator gels, hydroxyethyl cellulose and solid polymer electrolyte enzyme gels clearly demonstrated the principle of performing biocatalytic electrochemical reactions in the gas phase. However, the described methods suffered the problems of either low ionic conductivity or biocompatibility over relatively short periods of time. The novel support media of this invention which permit extended ionic conductivity and biocompatibility for relatively longer periods are now exemplified. The support media of the invention proved unexpectedly good with respect to ionic conductivity and biological compatibility. Other surprising features of the material will also be discussed.

Example 4

Ionically conducting gels of tetrabutylammonium toluene-4-sulfonate with incorporated polyphenol oxidase cast onto an array of interdigitated microband electrodes for reaction with phenol vapours.

In this example, an ionically conducting gel matrix formed by tetrabutyl ammonium toluene-4-sulfonate and sodiumphosphate buffer incorporating polyphenol oxidase is described. In this example, the enzyme proved to be relatively stable for a number of hours within the gel matrix. The indicator reaction was identical to that in example 2.

Experimental

Figure 9:
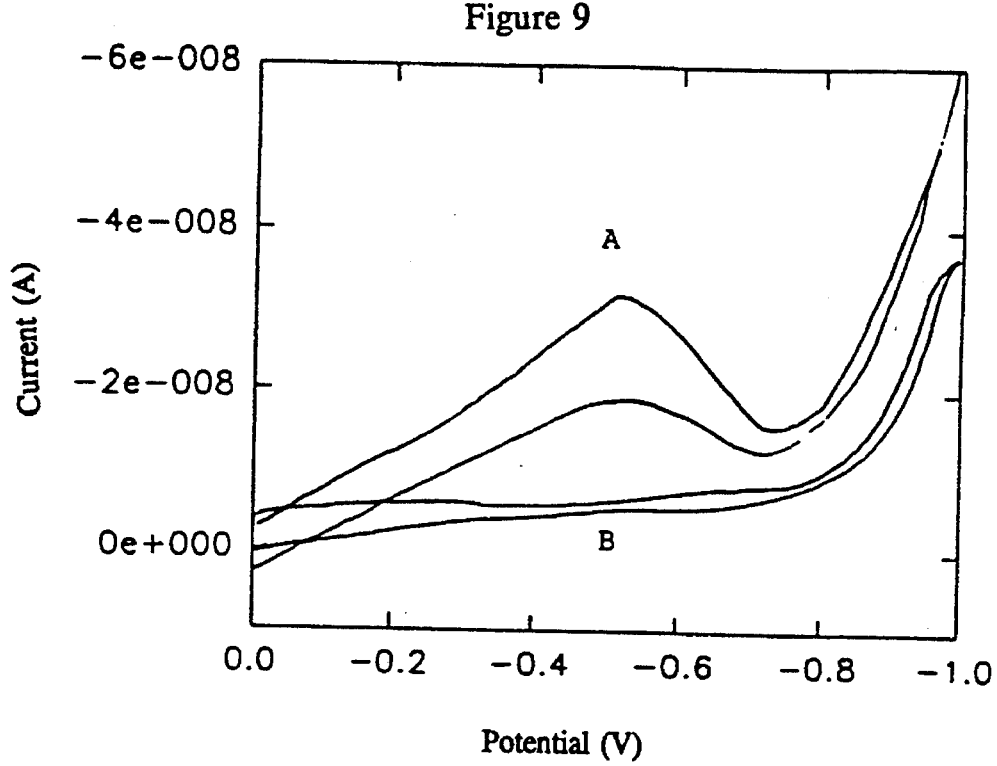
FIG. 9 shows a cyclic voltammogram at 0.005 V/s of (A) TBATS-polyphenol oxidase gel electrode and (B) TBATS gel only electrode in the presence of p-cresol vapours.

Tetrabutylammonium toluene-4-sulfonate (TBATS), Toluene-4-sulfonic Tetrabutylammonium salt, $(CH_3CH_2CH_2CH_2)_4N(CH_3C_6H_4SO_3)$, M, 413.67, (500 mg) was crushed in a mortar and pestle to form a powder and then placed in a glass bottle containing a 3 mλ volume of sodiumphosphate buffer (0.1 M, pH 7) and potassium chloride (0.05 M). The mixture was gently heated until the TBATS material was completely dissolved. The mixture was then sonicated for a period of 5 minutes. Polyphenol oxidase (1 mg) was then added to 100 μl TBATS solution and the resulting mixture vigorously stirred for 2 minutes on a rotator. A 5 μl of the TBATS-enzyme solution mixture was then placed onto the microband area of the electrode and allowed to air dry for 30 minutes. Following this period, the gel that had formed was immobile on electrode inversion. Cyclic voltammograms at 0.005 V/s in the absence and presence of p-cresol vapours were then recorded. The potential was cycled from 0 V to −1 V versus the CC + QRE. The results are illustrated in FIG. 9. In the presence of phenol vapours a reductive peak was evident at approximately −0.5 V versus the CC + QRE corresponding to the reduction of the quinone product of the enzyme reaction. (A) represents the cyclic voltammogram of the TBATS polyphenol oxidass gel electrode and (B) the TBATS gel only electrode, in the presence of pcresol vapours. The potential was cycled from 0 V to −1 V versus the CC + QRE.

In amperometric experiments the working potential was set at −0.65 V versus the combined counter and quasi-reference electrodes. Following an initial drying period of 30 minutes after gel casting, the modified electrode was exposed to p-cresol vapours for 100 second intervals with similar time periods of no exposure.

Figure 10:
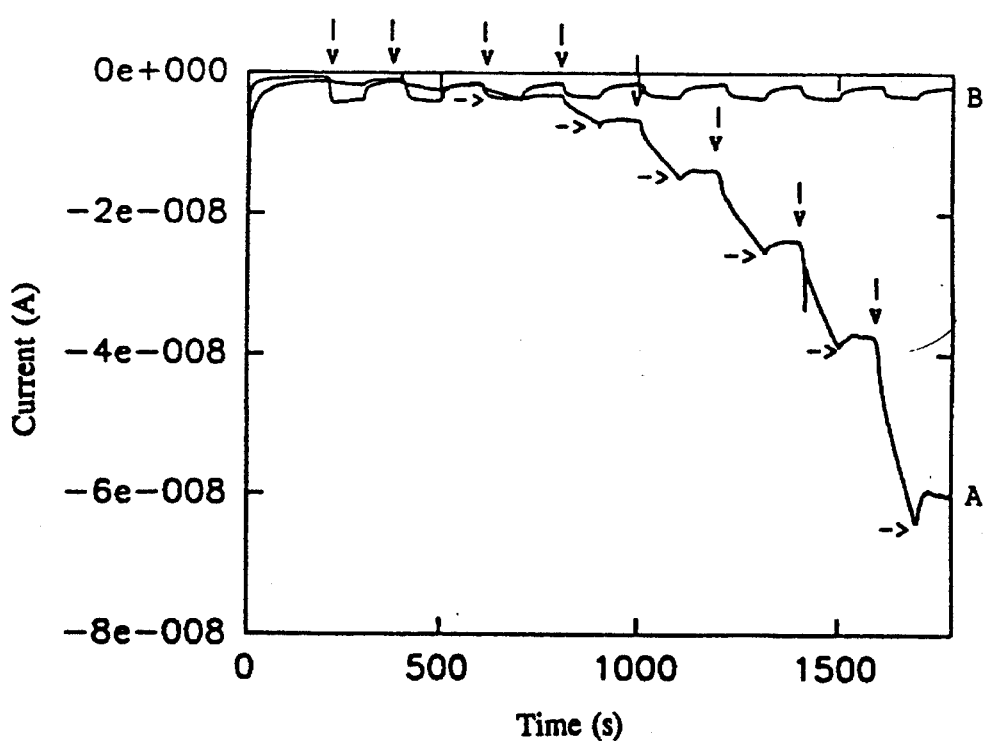
FIG. 10 shows an amperometric trace of (A) TBATS-polyphenol oxidase gel electrode and (B) TBATS gel only electrode with 100 second exposures to p-cresol with similar time intervals of no exposure.

These results are recorded in FIG. 10 which shows an amperometric trace of (A), the TBATS-polyphenol oxidass gel electrode and (B), the TBATS gel only electrode with 100 second exposures to p-cresol with similar time intervals of no exposure. The arrow indicates the start of the exposures. The potential of the working electrodes was 0.650 V versus the combined counter and quasi-reference electrodes.

Figure 11:
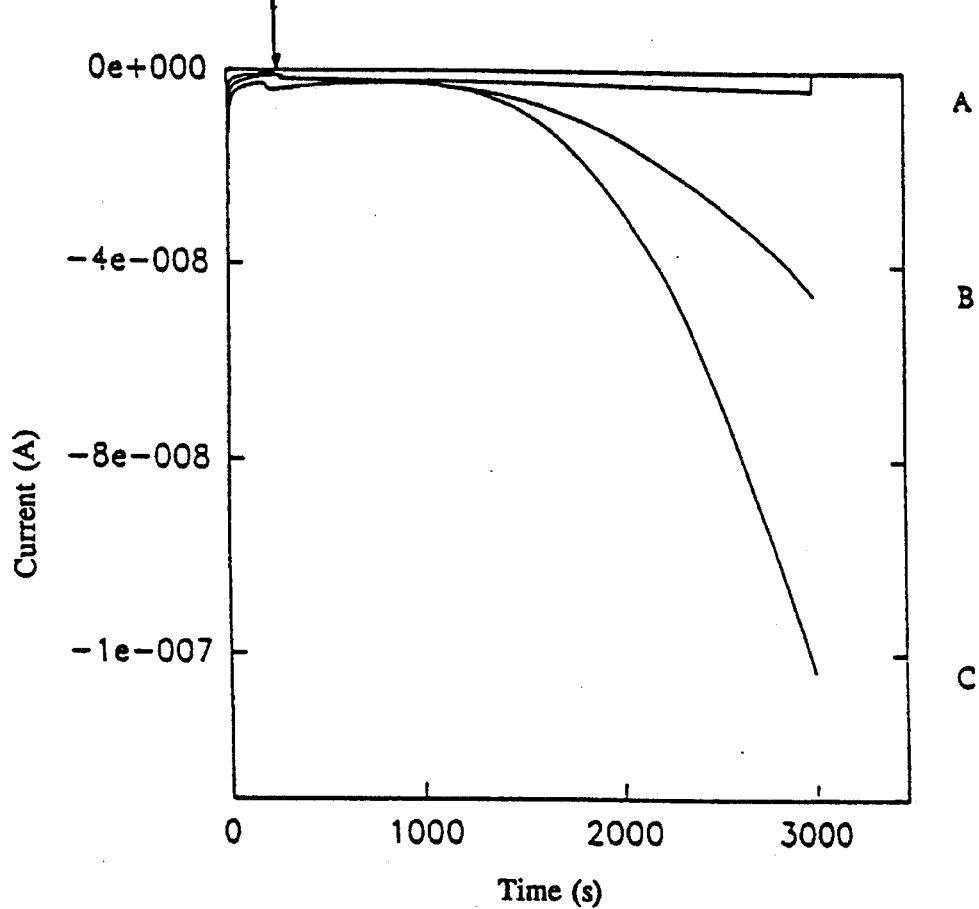
FIG. 11 shows an amperometric trace of TBATS gel electrodes with continuous exposure to p-cresol vapours, (A) TBATS gel only electrode after 48 hours storage at room temperature (18° C.), (B) TBATS-polyphenol oxidase gel electrode after 48 hours storage at room temperature and (C) TBATS-polyphenol oxidase gel electrode after 30 minutes drying at room temperature following gel casting.

To test the stability of the biocatalytic electrochemical gel media, an electrode was prepared and then left on the bench at room temperature for 48 hours before amperometric testing at 18° C. Following this period, an amperometric experiment was performed with continuous exposure to phenol vapours. The results are given in FIG. 11 which shows the amperometric trace of (A) TBATS gel only electrode; (B) TBATS-polyphenol oxidass gel electrode and (C) TBATS-polyphenol oxidass gel electrode after 30 minutes drying at room temperature following gel casting. The arrow indicates the start of the continuous exposure to p-cresol vapours. The potential of the working electrodes in all the experiments was −0.650 V versus the combined counter and quasi-reference electrodes.

In further tests, two microarray electrodes were coated with either a TBATS/water gel or a TBATS/ isopropanol (IPA) gel. The latter gel was dried in a heated drying cabinet at 72° C. for 30 minutes producing a thin film of TBATS on the surface of the electrode.

The modified electrodes were placed in a transparent petri-dish on the bench at room temperature for a number of weeks. For both TBATS/water and TBATS/IPA cast gels, a similar decrease in the ionic currents was seen after 60 days storage. No attempt was made to control temperature, light, humidity etc. The result was considered good with respect to the uncontrolled environmental conditions. It was thought that the hygroscopic propensity of TBATS may have contributed to the electrochemical stability. Following the storage period, the gel had formed a relatively rigid material that was difficult to remove from the electrode surface.

Example 5

Gaseous $H_2O_2$ reaction with horseradish peroxidase and potassium hexacyanoferrate (II) in tetrabutyl ammonium toluene-4-sulfonate gels cast onto an array of interdigitated microband electrodes.

The indicator reaction is identical to that described in example 1.

Experimental

Figure 12:
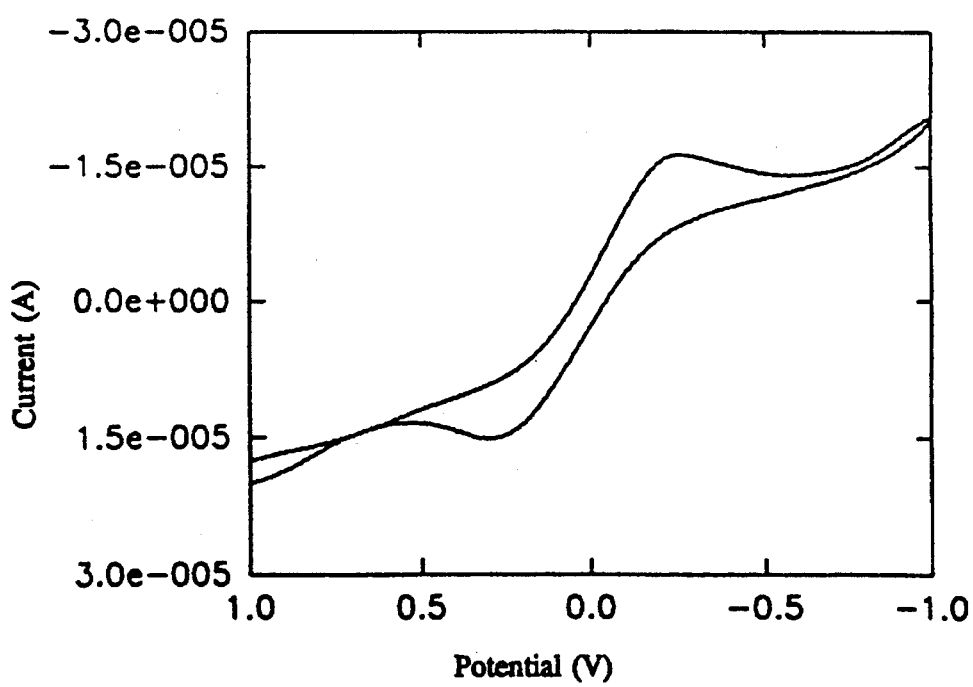
FIG. 12 shows cyclic voltammogram at 0.2 V/s of TBATS-horseradish peroxidase-potassium hexacyanoferrate (II) gel electrode.

A similar procedure to that used in the example 4 was implemented but using 2 mg of horseradish peroxidase and 500 mg TBATS / 3 ml of citric acid buffer (0.1 M, pH 6.5). A 5 μl volume of the enzyme-TBATS (2 mg/100 μl) solution was cast onto the microband section of the electrode and allowed to air dry at room temperature for 10 minutes. Following this drying period the enzyme formed a gel which was immobile on electrode inversion. A cyclic voltammogram at 0.2 V/s in which the potential was cycled from +1 V to −1 V versus the CC + QRE, following the drying period, revealed a reductive peak at approximately −0.25 V versus the CC + QRE. The results are shown in FIG. 12.

Figure 13:
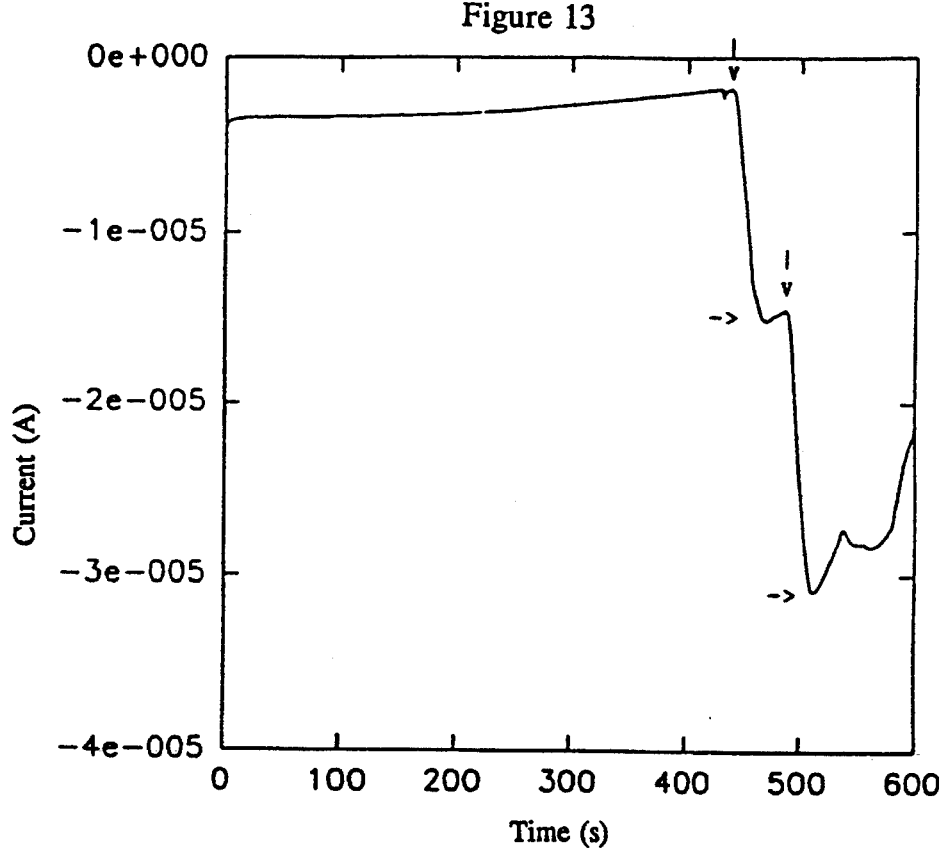
FIG. 13 shows an amperometric trace of TBATS-horseradish peroxidase gel electrodes. Solid arrows indicate exposure to gaseous $H_2O_2$.

Amperometric experiments were then carried out in which the gel-electrode was placed a distance of 5 mm from a 10 ml liquid solution of $H_2O_2$ in water (0.8 M) in a 25 ml glass beaker. The potential of the indicator electrode was set at −0.350 V versus the CC + QRE. The results are shown in FIG. 13. Solid arrows indicate exposure to gaseous $H_2O_2$. Broken arrows indicate no exposure. The increase in cathodic current on exposure to gaseous $H_2O_2$ was indicative of the reduction of the oxidised form of mediator following the enzyme reaction with $H_2O_2$.

Example 6

Phenolic Compound Induced Structural Changes in TBATS Gels

The amperometric trace obtained with the TBATS-enzyme gel described in example 4 (FIG. 10) displayed a delay in the initial response to p-cresol exposure between 200–800 seconds. The experiment using phenol instead of p-cresol also displayed this lag. The observed "lag phase" was thought to be important and worth investigating further. Experiments with a TBATS-water gel loaded with the electron mediator, ferrocene (0.0125 M) was used to investigate the lag phase observed in amperometric determinations. A volume of 1.5 μl of the TBATS-water-ferrocene solution was deposited onto the microarray section of the electrode. Immediately, a cyclic voltammogram at 0.2 V/s and at a potential of from +1 V to −1 V was recorded that produced a non-peaked voltammogram representative of rapid diffusion of the electroactive probe, ferrocene, to the working microelectrodes. See FIG. 14.

Figure 15:
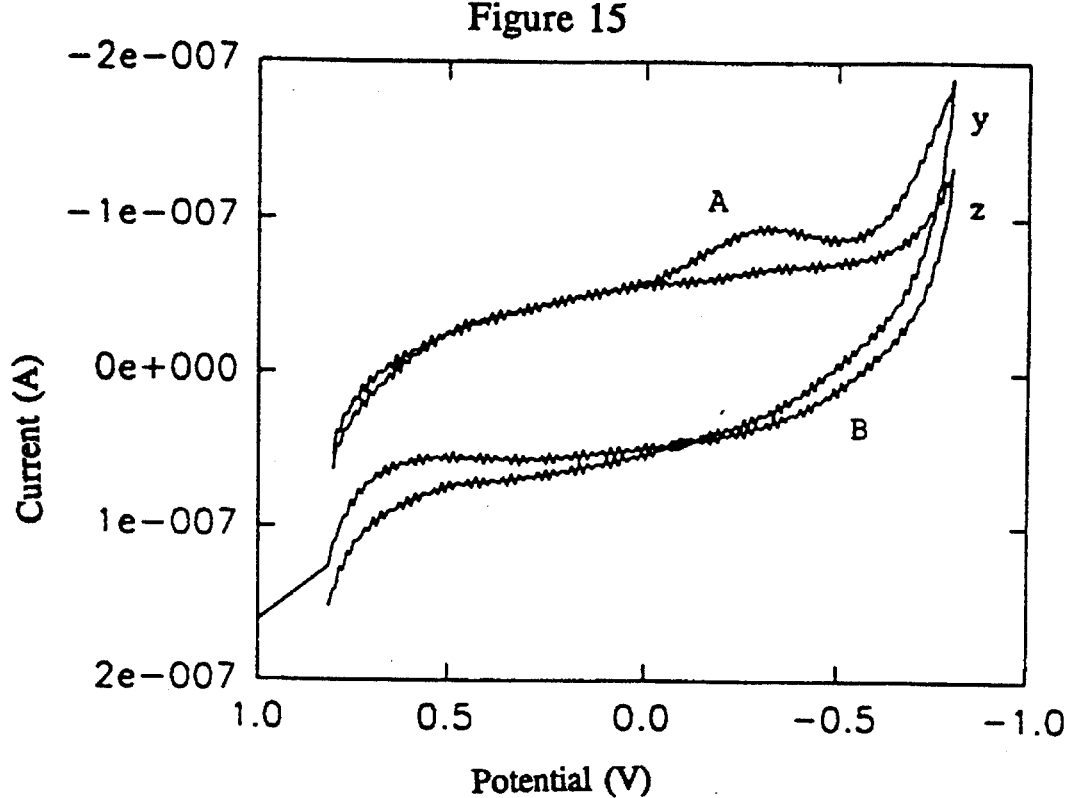
FIG. 15 shows a cyclic voltammogram at 0.2 V/s of TBATS-ferrocene gel electrode after (A) 7 minutes drying at room temperature and (B) 30 minutes drying at room temperature.

FIG. 15 illustrates the cyclic voltammograms at 0.2 V/s which were then recorded for a potential of +1 V to −1 V of TBATS-ferrocene gel electrode after (A) 7 minutes drying at room temperature and (B) 30 minutes drying at room temperature. Cyclic voltammograms were also recorded after 10, 16 and 24 minute intervals but the results are not illustrated.

Figure 14:
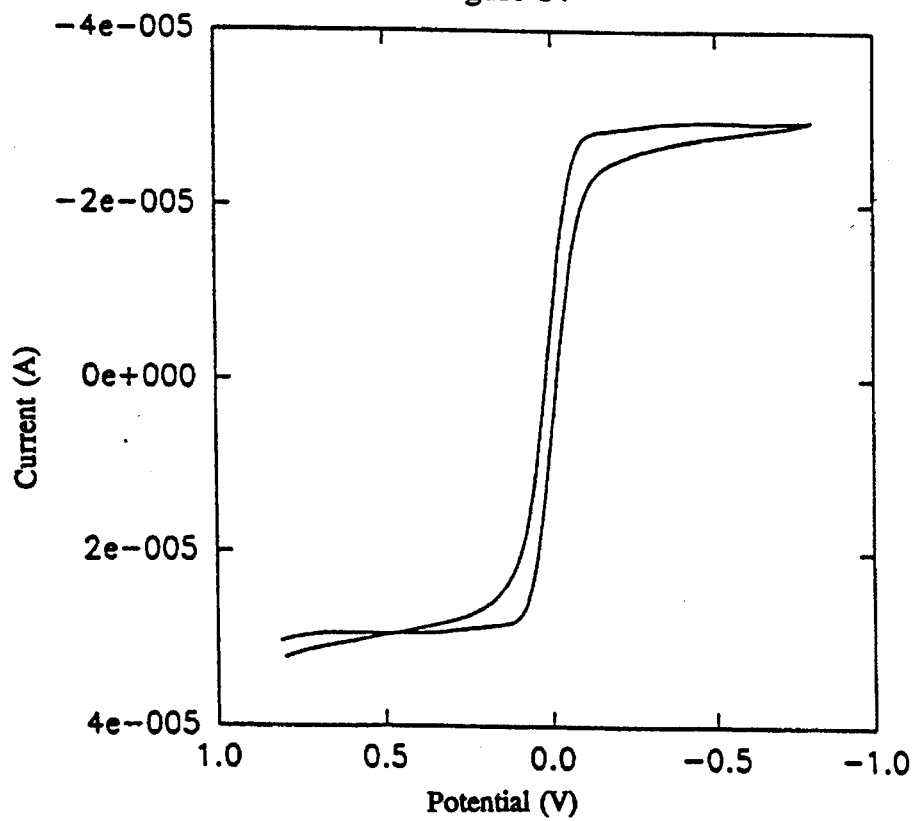
FIG. 14 shows a cyclic voltammogram at 0.2 V/s of TBAT-ferrocene gel electrode immediately following gel casting.

The clear change in voltammetric shape from FIG. 14 to FIG. 15 illustrates the reduced diffusion of the electroactive probe as the gel presumably lost water and became more rigid.

The situation of particular interest where phenol vapour partitions into the gel and undergoes biocatalytic conversion was also investigated. A similar procedure to that used in the amperometric experiments was employed but monitoring the diffusion of mediator using cyclic voltammetry. Electroactive probe gel electrodes as used in the previous experiment after 30 minutes drying were exposed to p-cresol for 100 second intervals followed by a further 100 seconds of no exposure. Immediately proceeding an exposure to p-cresol, a cyclic voltammogram at 0.2 V/s, and a potential of from +1 V to −1 V was recorded at room temperature.

Figure 16:
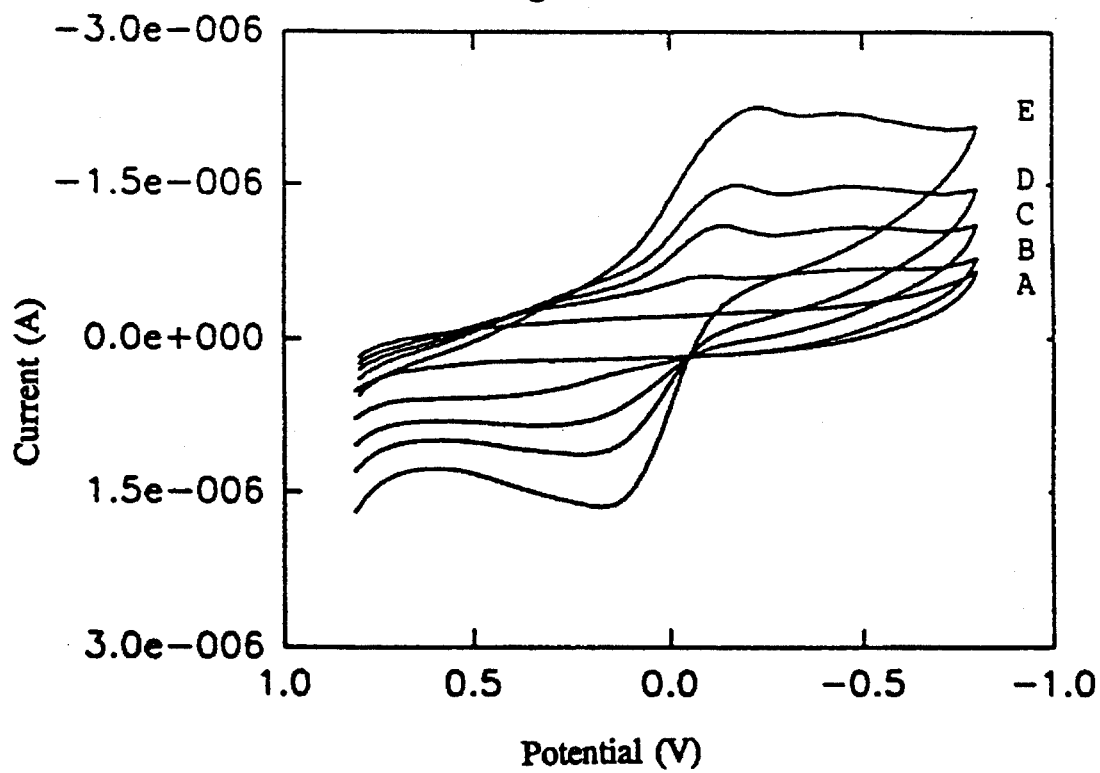
FIG. 16 shows cyclic voltammograms recorded approximately every 200 seconds at 0.2 V/s of TBATS-ferrocene gel electrode after 30 minutes drying time at room temperature followed by periodic exposure to p-cresol for 100 seconds with similar time intervals of no exposure. (A) represents the initial voltammogram at 0 seconds (after 30 minutes drying time); (B) after 200 seconds; (C) after 800 seconds; (D) after 1800 seconds; and (E) after 2200 seconds.

FIG. 16 shows a succession of cyclic voltammograms recorded approximately every 200 seconds at 0, 200, 800, 1800, and 2200 seconds. Letters indicate approximate times of recorded voltammograms (A) initial voltammogram after 30 minutes drying time; (B) after 200 s; (C) after 800 s; (D) after 1800 s; and (E) after 2200 s.

Peak currents increased in successive voltammograms and stabilised at around 2200 seconds. Distinct peaks began to form at around 800 seconds, a time approximating to the end of the lag phase observed in amperometric determinations (FIG. 10). The results suggested that the gel material underwent a structural change which facilitated the increased mobility of the electroactive probe on continued exposure to p-cresol. Again, repeating the experiment, replacing p-cresol with phenol produced the results qualitatively the same, but greater current magnitudes were obtained. Although plasticisation effects are well documented with respect to polymers, it was unclear how p-cresol induced the structural change within the TBATS gel. The precise structure of the TBATS gel was unknown to us but we anticipate an ordered matrix consisting of cationic and anionic groups of tetrabutylammonium and toluene-4-sulfonate ions respectively, interdispersed with water molecules.

One can further suggest p-cresol interfered with the electrostatic forces between the charged groups resulting in a loosening of the matrix structure and thus increased mobility of the electroactive probe. With respect to the amperometric enzyme electrode trace obtained in FIG. 10, we propose the diffusion coefficient of the product of the enzyme reaction increased on continued periodic exposure to p-cresol vapours as a consequence of increases in gel fluidity. No doubt substrate diffusion within the gel also increased but the effect would appear incidental since control electrodes, devoid of enzyme, produced fairly constant current increases as a result of non-specific conductivity changes induced by p-cresol.

Solvent Effects on the Support Matrix

Figure 17:
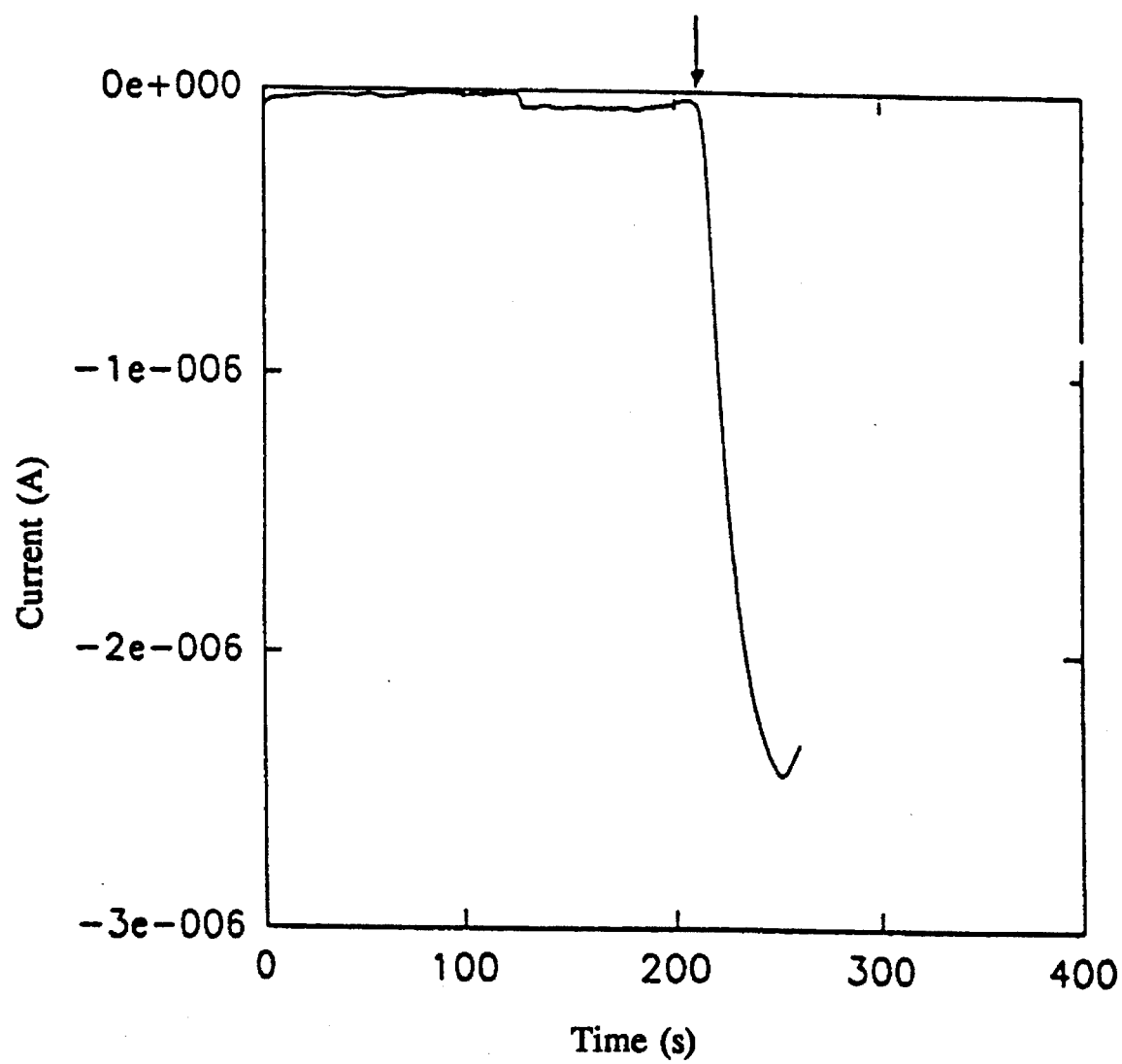
FIG. 17 shows an amperometric trace of TBATS-solvent cast polyphenol oxidase electrode.

Further experiments investigating the effect of casting solvent produced unexpected and intriguing results. TBATS material was dissolved in isopropanol and then cast onto the electrode surface and placed in a drying cabinet at 72° C. for 30 minutes. Following a further 5 minute drying period at room temperature, the TBATS gel was covered by a 5 μl volume of polyphenol oxidass-sodium phosphate buffer solution (1 mg/100 μl) and allowed to air dry for 15 minutes. When the electrode was exposed to p-cresol vapours, an immediate current increase was recorded. This is illustrated by FIG. 17 which shows an amperometric trace of TBATS solvent cast polyphenol oxidase electrode at −0.65 V. The solid arrow indicates the start of exposure to p-cresol.

It was proposed that the casting solvent played an important role in determining the structure of the TBATS gel matrix. It would appear that in the later case, the quinone product was able to move rapidly diffuse through the gel matrix and react at the electrode. It is thought that this is because the use of isopropanol solvent produces a thinner layer of matrix gel so that the diffusion through the gel is more rapid. However, in this situation it was likely that little solvent remained within the matrix following the high temperature drying procedure possibly resulting in a high density gel structure. This example of the manipulation of the structure and properties of the TBATS gels indicates how rapidly responding and stable matrices may be suitably produced for incorporation into analytical devices for the qualitative and quantitative determination of gaseous analytes.

We claim:

1. A method for determining a gaseous or vapor analyte comprising
   (1) providing a substantially liquid-free electrochemical cell comprising microvoltammetric electrodes including a microvoltammetric sensing electrode;
   solid or semi-solid support consisting essentially of an electrolyte in electrical contact with the microvoltammetric sensing electrode; and an enzyme or synzyme;

whereto the enzyme or synzyme is immobilized within the support in electrical contact with the microvoltammetric sensing electrode and wherein the enzyme or synzyme is contactable with a gaseous or vapor phase, and (2) exposing the electrochemical cell to a gaseous or vapor phase suspected of containing the gaseous or vapor analyte which is a substrate for the enzyme or synzyme, whereby the gaseous or vapor analyte contacts the enzyme or synzyme and reacts thereby generating a detectable electrical response relatable to presence of the analyte; and (3) determining the electrical response by the microvoltammetric sensing electrode to determine the presence or amount of the analyte.

2. A method according to claim 1 wherein the detectable electrical response increases on exposing the electrochemical cell to an increasing concentration of the analyte.

3. A method according to claim 1 in which the enzyme or synzyme is an enzyme for a redox reaction.

4. A method according to claim 1 wherein the solid or semi-solid support has a thickness no greater than 1 mm.

5. A method according to claim 4 in which the electrolyte is an organic salt.

6. A method according to claim 5 in which the organic salt comprises a tetrabutyl ammonium salt or a tetra ethyl ammonium salt.

7. A method according to claim 5 in which the organic salt is chosen from tetrabutyl ammonium perchlorate, tetrabutyl ammonium toluene-4-sulphonate, tetrabutylammonium methane sulphonate, tetrabutylammonium phenol borate, tetraethylammonium tetrafluoroborate, tetrabutyl-ammonium chloride and tetrabutyl ammonium iodide.

8. A method according to claim 4 in which the enzyme or synzyme is an enzyme for a redox reaction.

9. A method according to claim 1 wherein the support is formed from a hygroscopic electrolyte.

10. A method for determining a gaseous or vapor analyte comprising (1) providing a substantially liquid-free electrochemical cell comprising microvoltammetric electrodes including a microvoltammetric sensing electrode;

a solid or semi-solid support in electrical contact with the microvoltammetric sensing electrode; and an enzyme or synzyme;

whereto the support consists essentially of a solid or gel matrix formed from an electrolyte, wherein the enzyme or synzyme is retained by the support as an underlayer or overlayer for the support, and the support is in electrical contact with the microvoltammetric sensing electrode and whereto the enzyme or synzyme is contactable with a gaseous or vapor phase, and (2) exposing the electrochemical cell to a gaseous or vapor phase suspected of containing the gaseous or vapor analyte which is a substrate for the enzyme or synzyme, whereby the gaseous or vapor analyte contacts the enzyme or synzyme and reacts thereby generating a detectable electrical response relatable to presence of the analyte; and (3) detecting the electrical response by the microvoltammetric sensing electrode to determine the presence or amount of the analyte.

11. A method according to claim 10 wherein the enzyme or synzyme is retained by the support as an traderlayer for the support.

12. A method according to claim 10, said matrix comprising a solid or gel matrix formed from a tetraalkyl ammonium salt selected from tetrabutyl ammonium salts and tetraethylammmonium salts.

13. A substantially liquid-free support for a bioelectrochemical reaction comprising a solid or gel matrix comprising a tetra butyl ammonium salt or a tetra ethyl ammonium salt and an enzyme or synzyme, said matrix being permeable to a gaseous reactant, the reactant being a substrate for the enzyme or synzyme, wherein the enzyme or synzyme is retained by the support and wherein the enzyme or synzyme is contactable by the gaseous reactant.

14. A microvoltammetric sensing electrode comprising a conductor, a solid or semi-solid support m electrical contact with the conductor and an enzyme or synzyme retained by the support, the support consisting essentially of a solid or gel matrix of all electrolyte, wherein the enzyme or synzyme is immobilized within the support and the support is permeable to a gaseous reactant which is a substrate for the enzyme or synzyme and whereto the electrolyte is an organic salt.

15. An electrochemical sensor comprising sensing and counter electrodes, means for permitting access of analyte to the sensing electrode, and wherein the sensing electrode is as defined in claim 14.

16. A sensor according to claim 15 in which the sensing electrode and counter electrode are provided by an interdigitated microelectrode.

17. A sensing electrode according to claim 14 in which the organic salt is chosen from tetrabutyl ammonium perchlorate, tetrabutyl ammonium toluene-4-sulphonate, tetrabutylammonium methane sulphonate, tetrabutyl ammonium phenol borate, tetraethylammonium tetrafluoroborate, tetrabutylammonium chloride and tetrabutyl ammonium iodide.

* * * * *